United States Patent [19]

Noverola et al.

[11] 4,138,492
[45] Feb. 6, 1979

[54] AROMATIC AMIDES OF HETEROCYCLIC COMPOUNDS AND THERAPEUTIC COMPOSITIONS CONTAINING SAME

[75] Inventors: Armando V. Noverola; Jose P. Soto; R. G. W. Spickett, all of Barcelona, Spain

[73] Assignee: Anphar, S.A., Madrid, Spain

[21] Appl. No.: 558,908

[22] Filed: Mar. 17, 1975

[30] Foreign Application Priority Data

Mar. 21, 1974 [GB] United Kingdom ............... 12572/74

[51] Int. Cl.$^2$ .................. C07D 211/58; A61K 31/445
[52] U.S. Cl. .................................... 424/267; 544/335; 542/469; 546/197; 546/224; 546/194; 546/213; 546/187; 546/190; 546/233; 546/234
[58] Field of Search ...................... 260/293.58, 293.64, 260/293.73, 293.77; 424/267

[56] References Cited

U.S. PATENT DOCUMENTS

| 3,342,826 | 9/1967 | Miller et al. | 260/293.77 |
| 3,862,139 | 1/1975 | Podesua et al. | 260/293.77 |
| 3,879,401 | 4/1975 | Archibald et al. | 260/293.77 |
| 3,910,931 | 10/1975 | Cavalla et al. | 260/293.77 |
| 3,963,745 | 6/1976 | Cale et al. | 260/326.83 |

FOREIGN PATENT DOCUMENTS 1345872 2/1974 United Kingdom ................ 260/293.77

OTHER PUBLICATIONS

Harper et al., J. Med. Chem. 7: 729–732, (1964).
Newberry et al., C.A. 77: 151,956g, (1972).
Lamotte–Barrillon et al., C.A. 76: 67,982j, (1972).
Chemical Abstracts, vol. 83, (1975), 114199r, abstracting Ger. Offen 2, 316, 644 (1973).

Primary Examiner—Norma S. Milestone
Attorney, Agent, or Firm—Morgan, Finnegan, Pine, Foley & Lee

[57] ABSTRACT

The invention relates to aromatic amides N-substituted by heterocyclic groups. More particularly, the invention relates to substituted benzoic acid amides of 1-arylalkylamino or aminoalkyl-N-heterocyclic rings and to pharmaceutical compositions thereof, which have the ability to antagonize the effects of dopamine or dopaminergic agents of endogenous or exogenous origin and which may be used for the treatment of nausea and vomiting resulting from gastrointestinal disorders, congestive heart failure, post operative conditions, etc., other gastrointestinal disorders such as dyspepsia, flatulence, bile regurgitations, hiatus hernia, peptic ulcer, reflux aerophagitis, gastritis, duodenitis, and cholethiasis, and a variety of conditions affecting the central nervous system such as acute and chronic psychoses, maniacal psychosis, schizophrenias, serious disturbances of behavior and non-melancholic depressive state and migraine.

10 Claims, No Drawings

AROMATIC AMIDES OF HETEROCYCLIC COMPOUNDS AND THERAPEUTIC COMPOSITIONS CONTAINING SAME

SUMMARY OF THE INVENTION

According to our invention, in its broadest aspect, we provide a compound corresponding to the general formula (I):

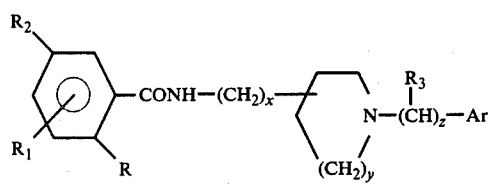

in which:
R is a lower ($C_1$–$C_6$) alkoxy or alkenoxy;
$R_1$ and $R_2$, which may be the same or different, are selected from hydrogen, halogen, sulphonamido, amino, lower ($C_1$–$C_6$) alkyl- or dialkylamino, alkylsulphonyl, alkylsulphonamido or acylamino groups, the radical $R_1$ being substituted at the 3 or 4 position of the aromatic ring;
$R_3$ is hydrogen, lower alkyl, or aryl;
Ar is aryl, aroyl, single ring heterocyclic group, or a group of the formula

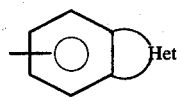

wherein Het is a heterocyclic ring;

x is 0 or 1;
y is an integer of from 2 or 3; and
z is an integer of from 1 to 6;
or a pharmaceutically acceptable salt thereof.

The acylamino group which may be present as the radical $R_1$ or $R_2$ or both may be represented by the formula ($R_4$CONH), where $R_4$ is hydrogen, lower alkyl, mono-, di- or trisubstituted halogen-lower-alkyl, or an amino or substituted amino lower alkyl, e.g., where $R_4$ is

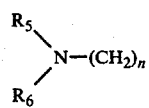

where n = 0–3 and $R_5$ and $R_6$ are hydrogen, lower ($C_1$–$C_6$) alkyl, arylalkyl or together with the nitrogen atom may form a 5, 6 or 7 membered ring which may or may not contain an additional heteroatom.

Illustrative examples of the acylamino group include formamido, acetamido, propionamido, chloroacetamido, trifluoroacetamido, aminoacetamido, 1-piperidylacetamido, ureido, N-alkylureido, butyramido, pentanoamido and hexanoamido.

The Ar group may be, for example, a phenyl or benzoyl group. Examples of single ring heterocyclic groups which may be present as Ar include thiophene, pyridine and pyrimidine. The Ar may also be a heterocyclic ring fused to a benzyl ring wherein the benzyl ring is directly attached to the

group. An example of such a heterocyclic ring fused to a benzyl ring is

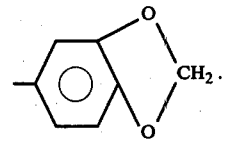

Each of the aryl, aroyl or heterocyclic groups represented by the radical $R_3$ or Ar may be substituted with 1 or 3 identical or different groups selected from the following: $C_1$–$C_6$-alkoxy, hydroxyl, amino, mono- or di-lower alkylsubstituted amino, nitro, halogen (fluoro, chloro or bromo) trifluoromethyl, $C_1$–$C_6$ straight or branched chain alkyl or sulphonamido. The number x is preferably 0 or 1.

A preferred group of compounds include N-arylalkyl piperidyl substituted benzamides which correspond to the general formula (I) wherein $R_1$ is substituted at the 4 position of the aromatic ring (i.e., phenyl ring); $R_2$ is halogen (i.e., chloro or bromo); R is a lower alkoxy or alkenoxy; x is 0; $R_1$ is preferably an amino group; y is 2;

is a saturated or unsaturated hydrocarbon present as a straight or branched chain alkyl or alkenyl residue containing up to six carbon atoms; and Ar is a substituted aryl of the formula

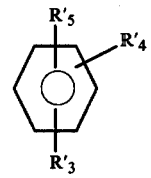

wherein $R'_3$, $R'_4$ and $R'_5$, which may be identical or different, are selected from hydrogen, halogen, lower alkoxy, hydroxy, nitro, amino, mono- or di-loweralkylamino, lower trifluoroalkyl or together two of them may be methylene dioxy.

Therefore, this preferred group of compounds may be defined by the more specific formula

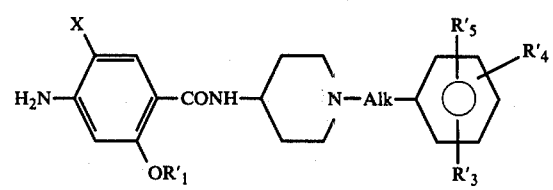

where

X is chloro or bromo;

$R'_1$ is lower alkyl or alkenyl;

Alk is a straight or branched chain alkyl or alkenyl residue containing up to six carbon atoms; and $R'_3$, $R'_4$ and $R'_5$ are as hereinabove defined.

These preferred compounds may be described as N-[4'-(1'-aryl-alkyl) piperidyl]-4-amino-5-halo-2-alkoxy benzamides and derivatives thereof. These preferred compounds include the compound N-[4'-(1'-benzyl)-piperidyl]-2-methoxy-4-amino-5-chloro-benzamide, [also named 4-amino-N-(-1-benzyl-4-piperidyl)-5-chloro-o-anisamide] which has been given the name Clebopride by the World Health Organization.

In another aspect of the invention, we provide a pharmaceutical composition, comprising a compound corresponding to the general formulas (I) and (I-A) as defined above, together with a pharmacologically acceptable carrier or diluent.

DETAILED DESCRIPTION OF THE INVENTION

Preparation of Compounds

The compounds of the invention may generally be prepared by reacting in an inert solvent the acid chloride of a substituted benzoic acid (II), where R, $R_1$, $R_2$, $R_4$, $R_5$ and $R_6$ have the same significance as above, with the appropriate 1-arylalkyl N-heterocyclic ring (III), where $R_3$, Ar, x, y and z have the same significance as above. The acid chloride of the acid (II) may be prepared by reacting the acid with an acid chloride, e.g., thionylchloride, sulphonylchloride, phosphorylchloride or oxalylchloride, in an inert solvent.

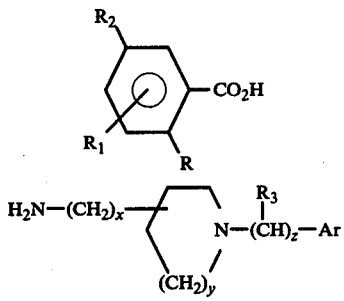

Compounds (I) may also be prepared by reacting the compound of structure (III) with a mixed anhydride of the substituted benzoic acid. The above reaction may be carried out in inert solvents at temperatures between ambient and 100° C. The mixed anhydride may be prepared in situ. At temperatures between −20 and +20° C., to substituted benzoic acid (II) is added a monoalkyl ester of carbonic acid, i.e., ethylchloroformate in the presence of a tertiary base, i.e., triethylamine or pyridine, etc., in an inert solvent to form the mixed anhydride. To this reaction mixture with a temperature between −20 and +20° C. the appropriate compound (III) is added.

The inert solvents which may be used in the above reactions include aromatic hydrocarbons, alkylketones, alkylesters, alkylethers, cyclic ethers, such as tetrahydrofuran and chlorinated hydrocarbons, etc.

The free amino compounds (I) in which $R_1$ or $R_2$ = $NH_2$ are prepared from the corresponding acylamino derivative (I) in which $R_1$ or $R_2$ is $R_4$—CONH, where $R_4$ = lower alkyl, trifluoromethyl or α-halogenoalkyl, by hydrolysis in either acidic or basic solution in solvents such as lower alcohols at temperatures between ambient and 100° C.

Arylaklyl derivatives (I), wherein $R_3$, z, and Ar are as previously defined, may also be prepared from the corresponding derivative of (I) in which the group

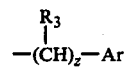

is replaced by hydrogen (Compound IV):

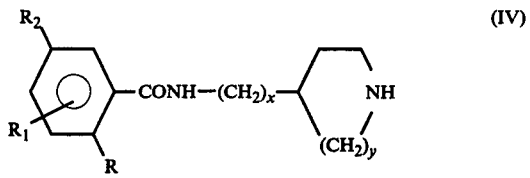

The compound (IV) is prepared by subjecting the corresponding benzyl compound (I) in which $R_3$ = H, z = 1 and Ar = phenyl to catalytic hydrogenolysis in a solvent such as a lower alcohol in the presence of a noble metal catalyst, e.g., palladium or platinum, which may be absorbed on an inert support such as carbon or barium sulphate, in the presence of hydrogen at normal or elevated pressure and at temperatures between ambient and 100° C. The compound (IV) may then be alkylated with the appropriate aralkyl chloride in the presence of a base such as sodium or potassium carbonate or sodium or potassium bicarbonate.

Amino acylamino compounds (I), where $R_1$ or $R_2$ = $R_4$CONH in which $R_4$ is

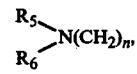

$R_4$, $R_5$ and $R_6$ having the same meaning as above, are prepared from the corresponding haloacyl derivative ($R_4$ = halogen-$(CH_2)_n$) by reaction with the appropriate amine in an inert solvent, such as an aromatic or aliphatic hydrocarbon, chlorinated hydrocarbon or aliphatic or cycloaliphatic ether at temperatures between ambient and 100° C.

The compounds of formula (I-A) of the invention may be prepared by reacting a 4-amino-5-halo-2-alkoxy benzoic acid, (in some cases after protecting the amino group with an acyl group such as acetyl, trifluoracetyl, chloracetyl, phthalyl, etc.), or an ester, acid halide, mixed anhydride or other active derivatives thereof, with a 4-amino-1-arylalkyl piperidine in an inert solvent at a temperature of from −20° C. to 150° C. depending on the method of condensation used. When a 4-acylamino-5-halo-2-alkoxy benzoic acid is used, the title compounds are liberated by acid hydrolysis of the acyl protecting group. .

In another embodiment, compounds (I-A) may be prepared by halogenation of N-[4'-(1'-arylalkyl)-piperidyl]-4-amino-2-alkoxy benzamides, prepared by one of the above methods, from a derivative of 4-amino-2-alkoxy-benzoic acid and 4-amino-1-arylalkyl-piperidine.

In still another embodiment, compounds (I-A) may be prepared by reacting an arylalkyl halide with N-[4'-piperidyl]-4-amino-5-halo-2-alkoxy benzamides (or their 4-acyl derivatives) in the presence of an inorganic or organic base in an inert solvent.

For example, 4-amino-5-chloro-2-methoxy benzoic acid may be converted into a mixed anhydride in situ with an alkyl chloroformate in the presence of a tertiary base, such as triethylamine or pyridine, in an inert solvent, such as a chlorinated hydrocarbon, a lower alkyl ester of a lower fatty acid, an alkyl ketone or ether, a cyclic ether such as tetrahydrofuran or dioxan, at a temperature of from −20° C. to room temperature; and the resulting mixed anhydride may then be reacted with 4-amino-1-benzyl piperidine to yield N-[4'-(1'-benzyl)-piperidyl]-4-amino-5-chloro-2-methoxy benzamide. This compound may also be prepared by condensing the same acid or a 4-acylamino derivative thereof with 4-amino-1-benzyl piperidine in the presence of a dehydrating agent such as silicon tetrachloride, a mono-, di- or trialkyl silyl halide, titanium tetrachloride, dicyclohexylcarbodiimide, thionylchloride or sulphur trioxide in dimethyl sulphoxide, toluene sulphonyl chloride, acetone dimethylacetal or a polymeric dehydrating agent. The reactions may be carried out in anhydrous inert solvents such as halogenated or aromatic hydrocarbons, pyridine, lower alkyl ketones, esters or ethers, or cyclic ethers at temperatures between room temperature and the boiling point of the solvent used. If an acyl protecting group is present, the compounds of formula (I-A) are obtained by acid hydrolysis.

Compounds of structure (I-A) may also be prepared by condensing lower alkyl esters of 4-acylamino-5-chloro-2-methoxy benzoic acid with 4-amino-1-arylalkyl piperidine in an inert solvent, such as an aromatic or chlorinated hydrocarbon, in the presence of a base, such as an alkali metal lower alkoxide or a trialkoxy derivative of aluminium with continuous removal of the lower alcohol formed in the reaction.

Another example of a reactive derivative of a 4-amino or 4-acylamino-5-halo-2-alkoxy-benzoic acid which may be used is, for instance, the derivative formed from N-ethyl-5-phenylisoxazoline 3-sulphonate (Woodwards Reagent).

The compounds (I-A) may also be prepared by reacting 4-acylamino-5-halo-2-alkoxy benzoic acid or its reactive derivatives, such as the acid chloride, N-imidazolamine or azide, with a 4-amino-1-arylalkyl piperidine. For example, 4-acetamido-5-chloro-2-methoxybenzoyl chloride reacts with 4-amino-1-benzyl piperidine in an inert solvent such as a halogenated hydrocarbon, an aromatic hydrocarbon, a lower alkyl ester of a lower alkonoic acid, a lower alkyl ketone or ether, or a cyclic ether, such as tetrahydrofuran or dioxan, in the presence of an organic tertiary base such as, for example, pyridine or a triethylamine, to give the 4-acetamido derivative, which may then be hydrolyzed in aqueous or aqueous alcoholic acid solutions to yield N-[4'-(1'-benzyl) piperidyl]-4-amino-5-chloro-2-alkoxy benzamide.

Compounds of structure (I-A) may also be prepared by reacting N-(4'piperidyl)-4-acylamino-5-chloro-2-alkoxy benzamides with arylalkyl halides in an inert solvent such as an aromatic hydrocarbon, lower alkyl ester of a lower alkanoic acid, lower alkyl ketone or ether or a cyclic ether, lower alkyl cyanide or chlorinated hydrocarbon, at temperatures between ambient and the boiling point of the solvent, in the presence of an inorganic base, such as potassium carbonate or sodium bicarbonate.

The 4-amino-5-halo-2-alkoxy benzoic acids used as starting material may be prepared from 4-acetamido salicylic acid by alkylation and esterification of the 2-hydroxyl group and the acid group respectively by treatment with a lower alkyl halide or sulphate in an inert solvent, such as a lower alkyl ketone or ester, in the presence of an inorganic base such as potassium carbonate. The product is then halogenated in the 5-position of the benzene nucleus with a halogen, such as chlorine or bromine, in a solvent, such as acetic acid, in the presence of the halide of a heavy metal, such as iron chloride. Other halogenating agents, such as iodobenzene dichloride, may also be used. The corresponding acid may be prepared by acid hydrolysis in aqueous or aqueous alcoholic solutions.

4-amino-1-arylalkyl piperidines may be prepared by reduction of the corresponding 1-arylalkyl piperidone oximes with alkali aluminium hydrides or alkali metals in an alcoholic solvent. [Harper N. J. et al. J. Med. Chem. 7, 729–732 (1964)].

1-arylalkyl 4-piperidone oximes may be prepared by reaction of the corresponding ketone with hydroxylamine hydrochloride in aqueous alcoholic solution. The 1-aryl-alkyl-4-piperidones are prepared by literature procedures [e.g., Beckett et al. J. Med. Pharm. Chem. 1, 37 (1959)] or from 4-piperidone hydrochloride. The latter compound is converted into its diethylene ketal with ethylene glycol. The ketal is then reacted with an aryl or arylalkyl acid halide to yield a 1-aroyl or 1-arylalkoyl piperidone ethylene ketal which may be reduced with lithium aluminum hydride to give the corresponding 1-arylalkyl piperidone diethylene ketal, acid hydrolysis of which yields the 1-arylalkyl-4-piperidone.

The invention also provides salts of compounds of structures (I) and (I-A) with biologically and pharmacologically acceptable inorganic and organic acids, non-limiting examples of which are sulphates; hydrohalide salts; phosphates; lower alkane sulphonates; arylsulphonates; salts of $C_1$–$C_{20}$ aliphatic mono-, di- or tribasic acids which may contain one or more double bonds, an aryl nucleus or other functional groups such as hydroxy, amino, or keto; salts of aromatic acids in which the aromatic nuclei may or may not be substituted with groups such as hydroxyl, lower alkoxyl, amino, mono- or di- lower alkylamino sulphonamido. Also included within the scope of the invention are quaternary salts of the tertiary nitrogen atom with lower alkyl halides or sulphates, and oxygenated derivatives of the tertiary nitrogen atom, such as the N-oxides. In preparing dosage formulations, those skilled in the art will select the pharmaceutically acceptable salts.

Compositions of the active compounds with pharmaceutically acceptable ingredients for oral and parenteral routes of administration are also included in the invention. The pharmaceutically acceptable diluents or carriers which are admixed with the active compound, or compounds, or salts of such compounds, to form the compositions of this invention are well known per se and the actual excipients used depend inter alia on the method of administering the compositions. The compositions of this invention may be adapted for oral, topical, percutaneous or parenteral use but the preferred method of administration is per os. In this case, the oral compositions may take the form of tablets, capsules, lozenges or effervescent granules or liquid preparations, such as mixtures, elixirs, syrups or suspensions, all containing one or more compounds of the invention; such preparations may be made by methods well known in the art.

The diluents which may be used in the preparation of the compositions include those liquid and solid diluents which are compatible with the active ingredients, together with coloring or flavoring if desired. Tablets or capsules may conveniently contain between 0.1 and 20 mgs and preferably 0.1 to 5 mgs of active component or the equivalent amount of its salts.

The liquid compositions adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or its salt or derivative in association with water, together with a suspending agent, flavoring agents, etc.

Compositions for parenteral injection may be prepared from soluble salts, which may or may not be freeze-dried and may be dissolved in water or an appropriate parenteral injection fluid.

In another aspect of the invention, the compounds may be mixed with other active anti-acid and anti-ulcer agents (excluding anticholinergic agents) for oral or in appropriate cases for parenteral use.

Therapeutic Properties

The compounds of the present invention have exhibited activities which may be considered beneficial in the treatment of gastrointestinal and cerebral malfunction in mammals including animals and man. The characteristic properties of these compounds are an antagonism of the effects of the dopaminergic agent, apomorphine, in animals, local anaesthetic activity and the ability to induce catatonia in rats and mice. Consequently, they are useful in the treatment of nausea and vomiting of diverse origin and as neuroleptic or tranquillizing agents.

Compounds provided by this invention have been shown to have antiemetic and neuroleptic properties and to increase the rate of stomach emptying in man. For example, salts of Clebopride have exhibited such properties at single doses of between 0.01 (10 μg) and 20 mg. They may be used in doses of from 0.1 to 1000 mg per day for the treatment of nausea and vomiting due to gastrointestinal disorders, congestive heart failure, post operative conditions, etc., other gastrointestinal tract disorders such as dyspepsia, flatulence, bile regurgitations, hiatus hernia, peptic ulcer, reflux aerophagitis, gastritis, duodenitis and cholethiasis, and as an adjunct to radiography of the gastrointestinal tract and for overcoming gastrointestinal stasis for diagnostic or therapeutic purposes and a variety of conditions affecting the central nervous system such as acute and chronic psychoses, maniacal psychosis, schizophrenias, serious disturbances of behavior and non-melancholic depressive state and migraine. The compounds cause considerably less disturbance in the central nervous system than does chlorpromazine or other phenothiazine anti-emetic agents, probably as a function of their more selective anti-dopaminergic effects.

Experimental tests have shown, for example, that the hydrochloride and malate salts of Clebopride are extensively metabolized in the rat and in the rabbit. Only very little of the unchanged drug is excreted in the urine. N-Debenzylation is a major metabolic reaction. Cleavage of the amide bond does not appear to be a major matabolic reaction. Conjugation with glucuronic acid and/or sulphate occurs at a large extent in the rabbit.

The pharmacokinetics of the drug after intravenous administration follows a similar pattern in both species. The relatively low plasma concentrations observed after oral administration of high doses of the malate salt in spite of rapidly appearing peak levels indicating good absorption, and the rapid appearance of metabolites in blood, suggest that extensive first pass metabolism and/or uptake take place in the liver.

The recognition of this phenomenon is important for the evaluation of the pharmacology and the toxicology of the drug and for the choice of optimal therapeutic doses for oral and parenteral administration.

Standard pharmacological tests have been run using many of the compounds defined by the generic structural formulae (I) and (I-A). These tests have been run with rats, mice, dogs and humans. In many of these tests, the instant compounds have been compared with metoclopramide and other known therapeutic compounds which have properties similar to those compounds of the present invention.

A number of the compounds of the present invention were screened in parallel with metoclopramide for potential anti-emetic effects against apomorphine-induced gnawing in the rat and as local anaesthetics on the rat sciatic nerve (Table I). The most active compounds were also tested for their ability to decrease gastric emptying time in rats. Compound number 2 (the hydrochloride salt of Clebopride) was shown to have a potency similar to that of metoclopramide in this test.

As can be seen from Table I, some of these compounds exhibit a similar profile of activity to metoclopramide and in particular, compound number 2 (Clebopride-HCl salt) and compound numbers 3, 8, 9, 12, 15 and 18 are more active as an anti-emetic.

Some of the compounds do not exhibit antiapomorphine activity in the rat even at high doses, but are active in antagonizing the effect of apomorphine in the dog and in the pigeon at doses of 10–100 μg/Kg and 10–50 mg/Kg respectively. Examples of such compounds are given by formula I where $R=OCH_3$, $R_1=H$, $R_2=SO_2NH_2$, $x=0$, $y=2$, $R_3=H$, $z=1$, $Ar=C_6H_5$; $R=OCH_3$, $R_1=H$, $R_2=SO_2C_2H_5$, $x=0$, $y=2$, $R_3=H$, $z=1$, $Ar=C_6H_5$.

The compounds cause considerably less disturbance in the central nervous system than does chlorpromazine and other phenothiazine antiemetic agents, This is demonstrated in Table III where it is shown that Clebopride, like metoclopramide and in contradistinction to chlorpromazine, exhibits antiemetic activity (anti-apomorphine activity) at doses which are far removed from those causing catatonia. The dose of the active compounds in humans may vary between 0.1 to 100 mg per day in divided doses.

The hydrochloride salt of Clebopride has demonstrated high activity against apomorphine-induced vomiting in the dog. Using the oral route, the hydrochloride salt is approximately 8 times more potent than metoclopramide as reported in Table II.

The properties of the compounds of the present invention are illustrated by the following discussion of pharmacological studies.

Based on pharmacological studies with mice, the HCl-Clebopride salt has shown to be a local anaesthetic with a potency somewhat greater than that of either metoclopramide or procaine.

Other studies have indicated that HCl-Clebopride effects the central nervous system. For example, it has anti-convulsant activity. Clebopride is somewhat more potent than metoclopramide in preventing electrically induced convulsions in mice. However, neither Clebopride nor metoclopramide appear to inhibit convulsions induced by strychnine in the mouse, nor to possess anti-oxotremorine activity. Nevertheless, both compounds are capable of causing salivation and tremors in mice which have been previously treated with a sub-threshold dose of oxotremorine. The HCl-Clebopride salt, but not metoclopramide, inhibits tonic convulsions (antileptazol) in the mouse but apparently not clonic seizures induced by leptazol.

Both HCl-Clebopride and metoclopramide inhibit spontaneous motor activity and cause incoordination as measured on an accelerating rota-rod in the mouse. Catatonia attributed to Clebopride has been noted in the rat and to a lesser extent in the mouse.

HCl-Clebopride salt has weak effects on the cardiovascular and respiratory systems. For example, in cats anaesthetized with chloralose, a slow-intravenous infusion of HCl-Clebopride salt at a rate of 1 mg/kg/min. to a total dose of 10 mg/kg produces a slight fall in both blood pressure and heart rate and slowing of respiratory movements.

HCl-Clebopride does not have an appreciable effect on the autonomic nervous system.

The HCl-Clebopride salt does have antipyretic and analgesic activity. For example, Clebopride in a 300/mg/kg per os dose had similar activity to 200 mg/kg of aspirin against yeast-induced pyresis in the rat. Clebopride, at a dose of 300 mg/kg per os, almost completely inhibited the writhing syndrome induced in mice by the intra-peritoneal injection of acetic acid.

The HCl-Clebopride salt has weak anti-inflammatory activity and no appreciable parasympatholytic activity.

A number of the instant compounds, particularly the hydrogen chloride, malate and methanesulfonate salts of Clebopride have been extensively tested in humans to determine maximum dosages and the therapeutic effects of the compounds. These compounds have been administered to humans orally and parenterally.

Suitable doses of the hydrochloride salt have been shown to be virtually free of side effects and single doses of between 0.2 and 5 mg appear to be effective in, for example, increasing gastric emptying. Dosages of between 0.1 and 30 mg per day have been shown useful depending upon the length of treatment and therapeutic effect desired.

TABLE I

FORMULA I

| No. | R | $R_1$ | $R_2$ | X | Y | $R_3$ $-(CH)_2-Ar$ | Antiapo-morphine* in rat | Local Anes. (1%) | Cat-atonia rats | $ED_{50}$ Values (mg/kg per os) |
|---|---|---|---|---|---|---|---|---|---|---|
| 1 | $OCH_3$ | $4-NHCO-CH_3$ | Cl | 0 | 2 | $CH_2-C_6H_5$ | +++ | + | + | ≈25 |
| 2 | $OCH_3$ | $4-NH_2$ | Cl | 0 | 2 | $CH_2-C_6H_5$ | ++++ | + | + | ≈3 |
| 3 | $OCH_3$ | $4-NH-CO-CH_2-Cl$ | Cl | 0 | 2 | $CH_2-C_6H_5$ | ++++ | + | + | <25 |
| 4 | $OCH_3$ | $4-NH-CO-CH_2-N\langle\rangle$ | Cl | 0 | 2 | $CH_2-C_6H_5$ | +++ | + | + | ≈12 |
| 5 | $OCH_3$ | $4-NH-CO-CH_2-Cl$ | H | 0 | 2 | $CH_2-C_6H_5$ | ++ | + | + | |
| 6 | | $4-NH-CO-CH_2-Cl$ | H | 0 | 2 | $CH_2-C_6H_5$ | + | + | N.t. | |
| 7 | $OCH_3$ | $4-NH-CO-CF_3$ | H | 0 | 2 | $CH_2-C_6H_5$ | ++ | + | + | <25 |
| 8 | $OCH_3$ | $4-NH_2$ | H | 0 | 2 | $CH_2-C_6H_5$ | ++++ | + | N.t. | <25 |
| 9 | $OCH_3$ | $4-NH-CO-CF_3$ | Cl | 0 | 2 | $CH_2-C_6H_5$ | +++++ | + | + | <25 |
| 10 | $OCH_3$ | H | Cl | 0 | 2 | $CH_2-C_6H_5$ | + | + | + | |
| 11 | $OCH_3$ | $NH_2$ | Cl | 1 | 2 | $CH_2-C_6H_5$ | ++ | + | N.t. | |
| 12 | $OCH_3$ | $NH_2$ | Cl | 0 | 2 | $CH_2-C_6H_4-4-Cl$ | +++++ | + | + | |
| 13 | $OCH_3$ | $NH_2$ | Cl | 0 | 2 | $CH_2-C_6H_4-3-OCH_3$ | ++ | + | + | |
| 14 | $OCH_3$ | $NH_2$ | Cl | 0 | 2 | $CH_2$-thiophene | +++ | + | + | |
| 15 | $OCH_3$ | $NH_2$ | Cl | 0 | 2 | $CH_2$-benzodioxole | ++++ | + | + | |
| 16 | $OCH_3$ | $NH_2$ | Cl | 0 | 2 | $CH_2CH=CH-C_6H_5$ | ++ | + | + | |
| 17 | $OCH_3$ | $NH_2$ | Cl | 0 | 2 | $CH_2-C_6H_4-3-Cl$ | +++ | + | + | |
| 18 | $OCH_3$ | $NH_2$ | Cl | 0 | 2 | $CH_2-C_6H_4-4-OCH_3$ | +++++ | + | + | |
| 19 | $OCH_3$ | $NH_2$ | Cl | 0 | 2 | $CH=(C_6H_5)_2$ | + | + | N.t. | |
| 20 | $OCH_3$ | $NH_2$ | Cl | 0 | 2 | $CH_2C_6H_4-2-OCH_3$ | ++ | + | N.t. | |
| 21 | $OCH_3$ | $NH_2$ | Cl | 0 | 2 | $CH_2C_6H_4-2-Cl$ | ++ | + | N.t. | |
| METOCLOPRAMIDE | | | | | | | +++ | + | + | ≈6 |
| CHLORPROMAZINE | | | | | | | ++++ | + | + | |

*Antiapomorphine activity in rat scored as follows:
+ active at 50 mg/Kg
++ active at 25 mg/Kg
+++ active at 12.5 mg/Kg
++++ active at 6.25 mg/Kg
+++++ active at 3.125 mg/kg

TABLE II

Protective effects of HCl-Clebopride salt and Metoclopramide against apomorphine induced vomiting in the dog.

| Compound | $ED_{50}$ mg/kg per os (95% confidence limits) |
|---|---|
| HCl Clebopride | 43.5 (22.29 – 84.88) |
| Metoclopramide | 343 (188.04 – 625.63) |

TABLE III

| Compound | Antiapomorphine Activity, Rats ED$_{50}$ mg/kg per os (95% confidence limits) | Catatonia Rats ED$_{50}$ per os (95% confidence limits) |
|---|---|---|
| Clebopride | 1.85 (1.48–2.04) | 47.58 (79.46–28.37) |
| Metoclopramide | 11.8 (10.58–13.15) | 93.01 (170.34–50.79) |
| Chlorpromazine | 7.95 (6.28–10.07) | 12.28 (18.04–8.36) |

A study was made to test the effect of Clebopride on decreasing gastric emptying time in humans, using a variety of doses (0.2 mg, 1 mg, 2 mgs and 5 mgs) in comparison with 10 mgs of metoclopramide.

All drugs were given in liquid suspension by mouth, and the patients used had a variety of diagnoses but having in common some kind of gastric disturbance.

The evaluation was based on the subjective opinion of the radiologist in terms of the time required for the appearance of peristaltic waves and their capacity to evacuate. the stomach, according to the following scheme:

+: no effect
++: moderate effect
+++: good effect
++++: maximum effect

As a guide, 10–20 mgs metoclopramide gave an effect of +++.

The results obtained in some 35 patients are detailed in the following table:

| Doses | No. of Patients | + | ++ | +++ | ++++ |
|---|---|---|---|---|---|
| 0.2 mg = | 6 | 0 | 0 | 6 | 0 |
| 1 mg = | 6 | 1 | 2 | 3 | 0 |
| 2 mg = | 8 | 0 | 2 | 3 | 3 |
| 5 mg = | 9 | 0 | 2 | 0 | 7 |
| Control | 6 | 1 | 5 | 0 | 0 |

From this and other tests, it is concluded that 0.2 mg of Clebopride gives as rapid and forceful contraction of the stomach as 20 mgs of metoclopramide. Two mg of Clebopride has a more rapid onset of action and gives a more forceful contraction than 20 mg of metoclopramide.

Another study has been made to investigate the acute tolerance of the malate salt of Clebopride following intramuscular and intravenous administration in humans.

The subjects used were healthy male volunteers between 20 and 24 years of age and were divided into 8 groups and dosed with the test compound according to the following scheme:

Group I: 1 mg intramuscular per day for 5 days
Group II: 1.5 mgs intramuscular per day for 5 days
Group III: 2 mgs intramuscular per day for 5 days
Group IV: 0.25 mg intravenously per day for 5 days
Group V: 0.50 mg intravenously per day for 5 days
Group VI: 1 mg intravenously per day for 5 days
Group VII: 1.5 mgs intravenously per day for 5 days
Group VIII: 2 mgs intravenously per day for 5 days The parameters evaluated were subjective symptoms; psychic disturbances; neurological disturbances; autonomic symptoms; digestive disturbances; urogenital disturbances; skin and mucous membranes; pulse; blood pressure; temperature; other side effects; blood analysis—leucocytes formula, hemoglobin content, erythrocyte sedimentation rate, glucose, cholesterol, urea, hepatic function tests, transaminasas; and urine analysis—density, albumin, sediment.

Significant effects are summarized as follows:

1. Of the four subjects in Group I, one case of slight sleepiness was noted from the second day of treatment.
2. Tiredness, sleepiness and fatigue in three of the four subjects in Group II accompanied with slight depression.
3. Three of the four subjects in Group III showed sleepiness, fatigue and depression followed by euphoria.
4. Sleepiness, fatigue and depression of medium intensity were seen in many patients in Groups IV to VIII and appeared not to be dose dependent. Additionally, in Groups VII and VIII, some degree of sweating, hypersalivation and dryness of the mouth were variously seen.
5. The blood and urine analysis performed in Groups II and VII showed no significant variations.

The following examples illustrate the preparation of various compounds of the present invention and their formulation into therapeutic compositions.

EXAMPLE 1

2-methoxy-4-($\alpha,\alpha,\alpha$-trifluoroacetamido)-5-chloro-benzoic acid 2.65 gr. (0.037 mol)of chlorine dissolved in 50 ml of acetic acid were added to a suspension of 9 gr (0.034 mol) of 2-methoxy-4-($\alpha,\alpha,\alpha$-trifluoroacetamido) benzoic acid in 160 ml acetic acid, slowly maintaining the temperature between 15°–20° C.

At the end of the addition the reaction was kept at ambient temperature for 4 hours. The reaction mixture was then poured into ice-water when a white solid was precipitated, and was filtered and dried. It was then crystallized from acetone-ether to give 9.1 gr of crystals, m.p. 178°–180° C. yield 90%. Using the same procedure, the following acids were also obtained: 2-methoxy-4-acetamido-5-chloro benzoic acid — m.p. 208°–210° C., 2-methoxy-4-($\alpha$-chloro acetamido)-5-chloro-benzoic acid — m.p. 183°–185° C.

EXAMPLE 2

2-methoxy-4-($\alpha,\alpha,\alpha$-trifluoroacetamido)-5-chloro benzoyl chloride A mixture of 10 gr (0.033 mol) of 2-methoxy-4-($\alpha,\alpha,\alpha$-trifluoroacetamido)-5-chloro benzoic acid, 6.6 ml. of thionyl chloride and 15 ml of dry benzene was heated at 60°–70° C. for 4 hours. The resulting solution was poured into 50 ml of petroleum ether and the precipitated product was collected by filtration in the form of a colorless solid (9 gr), m.p. 91°–93° C. By the same procedure the following acid chlorides were obtained: 2-methoxy-4-acetamido-5-chlorobenzoyl chloride — m.p. 144°–145° C., and 2-methoxy-4-($\alpha$-chloroacetamido) -5-chlorobenzoyl chloride — m.p. 123°–125° C.

EXAMPLE 3

N-[4'-(1'-benzyl) piperidyl]-2-methoxy-4-($\alpha,\alpha,\alpha$-trifluoroacetamido)-5-chlorobenzamide hydrochloride A solution of 14.7 gr (0.046 mol) of 2-methoxy-4-($\alpha,\alpha,\alpha$-trifluoroacetamido)-5-chlorobenzoyl chloride in 100 ml of methylethylketone was added slowly maintaining the temperature at 0°–5° C., to a solution of 7.99 gr (0.042 mol) of 1-benzyl-4-amino piperidine in 75 ml of methylethylketone cooled to a temperature of 0°-5° C. After the addition had been completed, the reaction was maintained at the same temperature with stirring for 1 hour and finally at room temperature for 5 hours.

The solid which had precipitated was filtered, washed with methylethylketone and then crystallized from ethanol to give 20 gr of a white solid, m.p. 227°-228° C. (d). By the same procedure the following compounds were prepared: N-[4'-(1'-benzyl) piperidyl]-2-methoxy-4-acetamido-5-chlorobenzamide — m.p. 134°-135° C.; N-[4'-(1'-benzyl) piperidyl]-2-methoxy-4-(α-chloroacetamido)-5-chlorobenzamide hydrochloride — m.p. 178°-180° C.; N-[4'-(1'-benzyl) piperidyl]-2-methoxy-4-α-chloroacetamidobenzamide hydrochloride — m.p. 245°-246° C.

EXAMPLE 4

N-[4'-(1'-benzyl) piperidyl]-2-methoxy-4-(α,α,α-trifluoroacetamido) benzamide hydrochloride A solution 19.7 gr (0.075 mol) of 2-methoxy-4-(α,α,α-trifluoroacetamido) benzoic acid in 150 ml of dry tetrahydrofuran was cooled to −15 to −10° C.

Triethylamine 10.52 ml (0.075 mol) in 30 ml of dry tetrahydrofuran was slowly added, followed by 7.05 ml (0.075 mol) of ethyl chloroformate, also dissolved in dry tetrahydrofuran.

Stirring was maintained for 1 hour at −15 to −10° C. and then 14.26 gr (0.075 mol) of 1-benzyl-4-amino piperidine in 30 ml of tetrahydrofuran was added. The temperature of the reaction was allowed to reach ambient temperature with agitation and was maintained at this temperature for 6 hours, at the end of which the precipitate was filtered. The organic extracts were concentrated at low temperature, the residue was dissolved in chloroform and the solution was washed several times with water.

The chloroform extracts were concentrated at low temperature to yield a paste which dissolved in warm ether and allowed to crystallize, when a white solid, 27 gr m.p. 183°-185° C. was obtained. This material was dissolved in acetone and a saturated solution of hydrochloric acid in ethanol was added to give a slightly acid solution. The precipitated hydrochloride salt was recrystallized from methanol to give 28 gr of the hydrochloride m.p. 239° C.(d). By the same procedure the following were obtained:

N-[4'-(1'-benzyl) piperidyl]-4-(α-chloroacetamido) benzamide hydrochloride — m.p. 271° C. (d); N-[4'-(1'-benzyl) piperidyl]-2-methoxy-5-chlorobenzamide hydrochloride — m.p. 236°- 238° C.; N-[4'-(1'-benzyl) piperidyl]-2-methoxy-5-sulphamoylbenzamide hydrochloride — m.p. 175°-178° C.; N-[4'-(1'-benzyl) piperidyl]-2-methoxy-4-amino-5-chlorobenzamide — m.p. 193°-195° C.

EXAMPLE 5

N-[4'-(1'-benzyl)-piperidyl]-2-methoxy-4-aminobenzamide dihydrochloride 50 ml of NaOH (8N) were added to a solution of 13.93 gr (0.032 mol) of N-[4'-(1'-benzyl) piperidyl] 2-methoxy-4-(α,α,α-trifluoroacetamido) benzamide in 50 ml of ethanol, and the reaction mixture was stirred at ambient temperature for 3 hours, at the end of which time it was diluted with water and was extracted with chloroform. The chloroform extracts were dried, decolorized and concentrated at low temperature to give a residue which was dissolved in acetone. A saturated solution of HCl in ethanol was added to the acetone solution until the solution was slightly acid. The solid was collected and recrystallized from ethanol to give 12 gr of a white product m.p. 215°-217° C. By the same process the following compound was obtained:

N-[4'-(1'-benzyl) piperidyl]-2-methoxy-4-amino-5-chlorobenzamide — m.p. 193°-195° C.; HCl.H$_2$O m.p. 216°-219° C.

EXAMPLE 6

N-[4'-(1'-benzyl) piperidyl]-2-methoxy-4-(N'-methylureido) benzamide hydrochloride 6 gr (0.017 mol) of N-[4'-(1'-benzyl) piperidyl]-2-methoxy-4-aminobenzamide dissolved in 30 ml of acetone-ether was stirred at room temperature while 2.56 ml (0.034 mol) of methyl isocyanate in 10 ml of ether was added. The resultant reaction mixture was stirred at ambient temperature for 6 hours. The resulting white precipitate was filtered, 5.5 gr m.p. 185°-187° C. It was then converted to the hydrochloride which was crystallized from methanol to give a colorless solid (5.5 gr) m.p. 239°-241° C. (d).

EXAMPLE 7

N-[4'-(1'-benzyl) piperidyl]-2-methoxy-4-(methylsulphonamido) benzamide hydrochloride 1.05 ml (0.0132 mol) of methansulphonylchloride in 10 ml of dry benzene were slowly added to a solution of 4.2 gr (0.012 mol) of N-[4'-(1'-benzyl) piperidyl]-2-methoxy-4-amino benzamide in 50 ml of dry benzene. The reaction mixture ws stirred at ambient temperature for 4 hours, at the end of which time the precipitate was filtered and crystallized from ethanol to give 5.3 gr of pure product — m.p. 235°-237° C.

EXAMPLE 8

N-[4'-(1'-benzyl) piperidyl]-2-methoxy-4-α-(1''-piperidyl) acetamido-5-chlorobenzamide dihydrochloride A mixture of 11 gr (0.0244 mol) of N-[4'-(1'-benzyl) piperidyl]-2-methoxy-4-(α-chloroacetamido)-5-chlorobenzamide and 5.07 ml (0.0512 mol) of piperidine in 50 ml of dry benzene was refluxed for 12 hours. At the end of the reaction, the product was filtered and washed several times with benzene. The benzene extracts were washed with water, decolorized, dried and concentrated at low temperature to give a paste. The latter was dissolved in a mixture of warm ether - petroleum ether and allowed to crystallize when a white solid was obtained m.p. 135°-137° C. It was converted into the dihydrochloride in the usual manner, crystallizing from ethanol-acetone to give 11 gr of product m.p. 241°-243° C.

EXAMPLE 9

N-(4'-piperidyl) 2-methoxy-4-acetamido-5-chlorobenzamide hydrochloride

A solution of 10 gr (0.022 mol) of N-[4'-(1'-benzyl) piperidyl] 2-methoxy-4-acetamido-5-chlorobenzamide hydrochloride in 100 ml of ethanol was agitated with hydrogen at ambient temperature and atmospheric pressure in the presence of 1 gr of Pd/C. (10%). After 8 hours the theoretical quantity of hydrogen had been absorbed, the catalyst was filtered and the filtrate was evaporated to dryness. The residue was crystallized from methanol-acetone and finally from ethanol to give 7 gr of product, m.p. 228°-230° C. The following compounds were prepared by the same procedure: N-(4'-piperidyl) 2-methoxy-4-amino-5-chlorobenzamide — m.p. 168°-170° C. and N-(4'-piperidyl) 2-methoxy-5-sulphamoylbenzamide hydrochloride m.p. 249°-250° C.

EXAMPLE 10

N-[4'-(1'-3''p-fluorobenzoylpropyl) piperidyl]-2-methoxy-4-acetamido-5-chlorobenzamide hydrochloride A mixture of 4 gr (0.0122 mol) of N-(4'-piperidyl)-2-methoxy-4-acetamido-5-chlorobenzamide, 2.695 gr (0.0134 mol) of 4-chloro-p-fluorobutyrophenone, 1.134 gr (0.0135 mol) of sodium bicarbonate, a crystal of potassium iodide and 70 ml of dry toluene was refluxed for 3 days, at the end of which time the inorganic products were filtered and washed with chloroform. The organic extracts were evaporated at low temperature to give a residue which was dissolved in acetone and converted to the hydrochloride by addition of HCl in ethanol. The product was crystallized from methanol to give 4.5 gr m.p. 195°-197° C. By the same procedure the following product was also obtained: N-[4'-(1'-phenylethyl)-piperidyl]-2-methoxy-4-acetamido-5-chlorobenzamide hydrochloride, m.p. 222°-223° C.

EXAMPLE 11

4-acetamidosalicylic acid 30.6 grs (0.2 mol) p-aminosalicylic acid and 100 cc ethanol were introduced into a 250 ml flask, and the mixture was heated to 40° C. 20.4 grs (0.2 mol) acetic anhydride was then added at such a rate that the temperature did not exceed 50° C. When the addition was complete, the mixture was stirred at 50° C. for 3 hours. The product was filtered. Weight: 36 grs m.p. = 235° C. Yield = 92%.

EXAMPLE 12

Methyl 2-methoxy-4-acetamidobenzoate 34 grs (0.17 mol) 4-acetamidosalicylic acid, 57.96 grs (0.42 mol) $K_2CO_3$ and 250 ml acetone were introduced into a 500 cc flask and heated to 40° C. Then, maintaining the same temperature, 51.40 grs (0.408 mol) methyl sulphate was added in approximately 15 minutes, and the mixture was heated under reflux for 5 hours. The mixture was cooled, the $K_2SO_4$ precipitate was filtered and the acetone solution was concentrated to ⅓ of its original volume. Dilution with ethyl ether gave a crystalline solid which was filtered, weight 34 grs. m.p. = 130°-132° C. Yield = 89%.

EXAMPLE 13

Methyl 2-methoxy-4-acetamido-5-chlorobenzoate 34.8 grs methyl 2-methoxy-4-acetamidobenzoate, 180 ml acetic acid and a trace of $FeCl_3$ were introduced into a 500 cc flask, provided with an agitator, a thermometer and a gas inlet. The solids were dissolved by heating and the solution was cooled to 15° C. Maintaining this temperature, a current of chlorine was passed through the solution, the reaction being controlled by cooling, until the weight had increased by 11.2 grs. The solution obtained was poured into 2 liters of water, precipitating a white solid, which was filtered to yield 33 grs of product. m.p. = 149°-152° C. Yield = 82%.

EXAMPLE 14

2-methoxy-4-amino-5-chloro benzoic acid 25.75 grs (0.1 mol) methyl 2-methoxy-4-acetamido-5-chlorobenzoate were introduced into a 500 ml flask, suspended in 100 ml ethanol. 40 grs NaOH, dissolved in 150 cc of water, were added and the mixture was heated under reflux for 2.5 hours. The mixture was diluted with water and made acid with concentrated HCl. The white solid which precipitated was collected and recrystallized from methanol. Weight: 17 grs m.p. = 213°-215° C. Yield = 84%.

EXAMPLE 15

1-benzyl-4-piperidone-oxime 48 grs 1-benzyl-4-piperidone oxime hydrochloride(1) were placed in a liquid-liquid extraction apparatus, and dissolved in a solution of 8 grs NaOH in 100 ml water. After 7 hours of extraction with ether, 38 grs white solid were obtained. m.p. = 129°-131° C. Yield = 93%.
(1) P. Brookers, R. J. Terry and Walker. J. Chem.Soc. 3172 (1957).

EXAMPLE 16

1-benzyl-4-amino-piperidine 7.6 grs (0.2 mol) lithium aluminium hydride and 300 ml anhydrous ether were introduced into a 1 l. flask, provided with a mechanical agitator and a Soxhlet extractor. 20 grs (0.1 mol) 1-benzyl-4-piperidone oxime were placed in the Soxhlet cartridge, and the mixture was heated under reflux for 12 hours, at the end of which time the excess of $LiAlH_4$ was destroyed. The ethereal extracts were dried and concentrated to dryness giving an oil that weighed 18 grs. On distillation in vacuo 17 grs of pure product was obtained. b.p. = 103°-105° C. at 0.07 mmHg.

By a similar procedure the following compounds were prepared:

1-phenethyl-4-aminopiperidine dihydrochloride, m.p. 333°-335° C.;
1(m-methoxybenzyl)-4-aminopiperidine dihydrochloride, m.p. 240°-242° C.;
1(p-methoxybenzyl)-4-aminopiperidine dihydrochloride, m.p. 257°-259° C.;
1(m-chlorobenzyl)-4-aminopiperidine dihydrochloride, m.p. 275°-276° C.;
1(p-chlorobenzyl)-4-aminopiperidine dihydrochloride, m.p. 308°-310° C.;
1-cinnamyl-4-amino-piperidine, b.p. 106°-108/0'04 mm Hg;
1-piperonyl-4-amino-piperidine, m.p. 52°-53° C.;
1-(2'-thenyl)-4-amino-piperidine dihydrochloride, m.p. 259°-261° C.;
1(o-chlorobenzyl)-4-aminopiperidine dihydrochloride, m.p. 248°-250° C.;
1(3',4'-dichlorobenzyl)-4-aminopiperidine dihydrochloride, m.p. 288°-291° C.;
1(o-methoxybenzyl)-4-aminopiperidine dihydrochloride, m.p. 224°-225° C.;
1(diphenyl-methyl)-4-aminopiperidine, m.p. 88°-92° C.;
1(3',4'-dimethoxybenzyl)-4-aminopiperidine dihydrochloride, m.p. 229°-231° C.;
1(3', 4', 5' trimethoxybenzyl)-4-aminopiperidine, m.p. 42°-45° C.;

1(sec-phenethyl)-4-aminopiperidine dihydrochloride, m.p. 275°–277° C.; and

1(2'-methoxy-5'-chlorobenzyl)-4-aminopiperidine dihydrochloride, m.p. 255°–259° C.

EXAMPLE 17

N-[4'-(1'-benzyl)-piperidyl]-2-methoxy-4-amino-5-chloro benzamide (a) 16.5 grs (0.081 mol) 2-methoxy-4-amino-5-chloro benzoic acid, dissolved in 450 ml anhydrous tetrahydrofuran were introduced into a 1 l. flask, supplied with an agitator and an additional funnel. 11.4 ml (0.081 mol) triethylamine in 30 cc tetrahydrofuran were slowly added to this solution, maintaining it at room temperature. The mixture was then cooled to between 10° C. and 0° C., and 6.48 ml (0.089 mol) ethyl chloroformate in 15 ml tetrahydrofuran were added. After stirring for 1 hour, at the same temperature, 15.39 grs (0.081 mol) 1-benzyl-4-amino-piperidine, dissolved in 30 ml tetrahydrofuran, were added, maintaining the same temperature. When the addition was complete, the mixture was left at between 0° C. and 10° C. for 1 hour and then for 8 hours at room temperature. The triethylamine hydrochloride was filtered, and the organic phase was concentrated to dryness, leaving a white solid which was recrystallized from MeOH to yield 25.5 grs of pure product. m.p. = 193°–195° C. Yield = 84%.

(b) 34.5 grs (0.134 mol) of methyl-2-methoxy-4-acetamido-5-chloro benzoate, 67 ml of xylene, 26.63 grs (0.140 mol) of 1-benzyl-4-amino piperidine and 6.7 grs of aluminium isopropylate were placed in a 500 ml flask provided with an agitator and a Vigreux distillation column of approximately 30 cms height. The mixture was heated until the theoretical quantity of methanol had distilled. The excess of xylene was removed and the residue was treated with a mixture of 160 cc of water and 40 cc of concentrated hydrochloride acid. The xylene layer was removed and the aqueous solution was made alkaline with sodium hydroxide solution and extracted with chloroform. The chloroform extracts were concentrated and colorless solid which remained was collected, m.p. 134°–135° C.

This solid was heated under reflux with a solution of 134 cc of concentrated hydrochloride acid and 220 cc of water for 1 hour. At the end of this time, the solution was made alkaline with sodium hydroxide and was then extracted with chloroform. The chloroform extract was concentrated to yield a white solid, m.p. 193°–195° C., weight 37.5 grs (72%).

(c) To a solution of 8.04 gr of 4-amino-5-chloro-2-methoxy benzoic acid and 7.6 grs of 4-amino-1-benzyl piperidine in 100 ml of anhydrous pyridine as added 3.4 gr of silicon tetrachloride at room temperature. The mixture was then heated under reflux for 3 hours and the pyridine was removed in vacuo. The residue was then treated with a mixture of water and chloroform and agitated vigorously, when an insoluble residue separated. The clear liquid was decanted, and the aqueous phase was separated and made alkaline with a solution of sodium carbonate and then extracted with chloroform. The chloroform solution was dried and distilled to yield 12 gr of product m.p. 193°–195° C.

(d) To a solution of 4.0 gr of 4-amino-5-chloro-2-methoxy benzoic acid in 100 ml of methylene chloride was added at room temperature 4.1 gr of N,N'-dicyclohexylcarbodiimide. After a few minutes 3.8 gr of 4-amino-1-benzyl piperidine was added with agitation and the mixture was stirred at room temperature overnight.

The insoluble N,N'-dicyclohexylurea was removed by filtration and the filtrate washed with water, dried and the solvent removed in vacuo. The residue was recrystallized from methanol to yield 6.0 gr of product, m.p. 194°–195° C.

(e) To a solution of 4.90 grs of 4-acetamido-5-chloro-2-methoxy benzoic acid in 80 ml of pyridine was added 13 ml of benzenesulphonyl chloride followed by 1.9 gr of 4-amino-1-benzyl piperidine, and the mixture was stirred at room temperature for 1 hour. It was then poured onto a mixture of ice and water and the product was extracted with chloroform. The chloroform layer was separated, washed with water, dried and the solvent removed in vacuo. The residue was recrystallized from methanol to give 3.5 gr of the 4-acetamido compound, m.p. 134°–135° C. This compound was then hydrolyzed by the method given in Example 17(b) to yield pure produce, m.p. 194°–195° C.

(f) To a mixture of 2.5 gr of N-ethyl-5-phenylisoxazolinium 3-sulphonate (Woodward's reagent) in 25 ml of anhydrous acetonitrile was added, drop by drop, at a temperature of −5 to 0° C., a solution of 2.5 gr of 4-acetamido-5-chloro-2-methoxy benzoic acid in 40 ml of anhydrous tetrahydrofuran containing 0.75 ml of triethylamine. After the addition was completed, the mixture was agitated at 0° for one hour and at room temperature for a further hour. It was then cooled to −5 to 0° C. and a solution of 2 grs of 4-amino-1-benzyl-piperidine in 10 ml of anhydrous tetrahydrofuran was added. The resulting mixture was agitated at 0° for one hour and at room temperature for 3 hours and the solvent removed in vacuo. To the residue was added 40 ml of water, and the resulting solution was made alkaline with sodium hydroxide solution and then extracted with chloroform. The chloroform solutions were separated, dried and the solvent removed. The residue was crystallized from methanol to yield the product, m.p. 134°–135° C. This product was hydrolyzed by the procedure given in example 17(b) to yield the title compound, m.p. 193°–195° C.

By a procedure similar to that described in Example 17(a), the following compounds were prepared:

N-[4'-(1'-phenethyl)-piperidyl]-2-methoxy-4-amino-5-chlorobenzamide hydrochloride, m.p. = 243°–245° C.;

N-[4'-(1'-m-methoxy-benzyl)-piperidyl]-2-methoxy-4-amino-5-chloro-benzamide hydrochloride, m.p. = 226°–227° C.;

N-[4'-(1'-p-methoxy-benzyl)-piperidyl]-2-methoxy-4-amino-5-chloro-benzamide hydrochloride, m.p. = 238°–239° C.;

N-[4'-(1'-m-chlorobenzyl)-piperidyl]-2-methoxy-4-amino-5-chloro-benzamide hydrochloride, m.p. = 204°–206° C.;

N-[4'-(1'-cinnamyl)-piperidyl]-2-methoxy-4-amino-5-chlorobenzamide hydrochloride, m.p. = 257°–259° C.;

N-[4'-(1'-piperomyl)-piperidyl]-2-methoxy-4-amino-5-chlorobenzamide hydrochloride, m.p. = 264°–266° C.;

N-[4'-(1'-[2''-thenyl]) piperidyl]-2-methoxy-4-amino-5-chloro-benzamide hydrochloride, m.p. = 231°–233° C.;

N-[4'-(1'-benzyl)-piperidyl]-2,4,5-trimethoxy-benzamide, m.p. =166°–170° C.;

N-[4'-(1'-benzyl)-piperidyl]-2-methoxy-4amino-5-bromobenzamide hydrochloride, m.p. = 180°–183° C.;

N-[4'-(1'-p-chlorobenzyl)-piperidyl]-2-methoxy-4-amino-5-chloro-benzamide hydrochloride, m.p. = 253°–256° C.;

N-[4'-(1'-diphenyl-methyl)-piperidyl]-2-methoxy-4-amino-5-chloro-benzamide hydrochloride, m.p. = 153°–159° C.;

N-[4'-(1'-o-methoxy-benzyl)-piperidyl]-2-methoxy-4-amino-5-chloro-benzamide, m.p. = 163°–165° C.;

N-[4'-(1'-o-chlorobenzyl)-piperidyl]-2-methoxy-4-amino-5-chloro-benzamide hydrochloride, m.p. = 221°–224° C.;

N-[4'-(1'-[3", 4"-dichlorobenzyl])-piperidyl]-2-methoxy-4-amino-5-chloro-benzamide hydrochloride, m.p. = 212°–214° C.;

N-[4'-(1'-[3", 4", 5"-trimethoxy-benzyl]) -piperidyl]-2-methoxy-4-amino-5-chloro-benzamide, m.p. = 80°–82° C.;

N-[4'-(1'-[3", 4"-dimethoxy-benzyl])-piperidyl]-2-methoxy-4-amino-5-chloro-benzamide, m.p. = 175°–178° C.;

N-[4'-(1'-sec-phenethyl)-piperidyl]-2-methoxy-4-amino-5-chlorobenzamide hydrochloride, m.p. = 247°–250° C.; and N-[4'-(1'-benzyl)-piperidyl]-2-methoxy-5-methylsulphonylbenzamide hydrochloride, m.p. = 206°–208° C.

EXAMPLE 18

N-[4'-(1'-benzyl)-piperidyl]-2-methoxy-4-amino-5-chlorobenzamide fumarate ($C_{20}H_{24}ClN_3O_2 \cdot C_4H_4O_4$)

A hot solution of 3.75 gr N-[4'-(1'-benzyl)-piperidyl]-2-methoxy-4-amino-5-chlorobenzamide in 130 ml methanol was added to a hot solution of 1.2 gr fumaric acid in 60 ml acetone and 20 ml methanol. The resulting solution was filtered and allowed to cool, when the product crystallized, yield 2.7 gr. m.p. 209°–210° C. Following a similar procedure, the following salts of N-[4'-(1'-benzyl) piperidyl]-2-methoxy-4-amino-5-chlorobenzamide were prepared:

| | | |
|---|---|---|
| Phosphate ($C_{20}H_{24}ClN_3O_2 \cdot PO_4H_3$) | m.p. | 224–225° C |
| Succinate ($C_{20}H_{24}ClN_3O_2 \cdot C_4H_6O_4$) | | 166–168° C |
| Citrate Monohydrate ($C_{20}H_{24}ClN_3O_2 \cdot C_6H_8O_7 \cdot H_2O$) | | 86–90° C (d) |
| Oxalate ($C_{20}H_{24}ClN_3O_2 \cdot C_2H_2O_4$) | | 234–235° C |
| α-ketoglutarate ($C_{20}H_{24}ClN_3O_2 \cdot C_5H_6O_5$) | | 113–115° C |
| Malate ($C_{20}H_{24}ClN_3O_2 \cdot C_4H_6O_5$) | | 170° C (d) |
| Hydrochloride monohydrate | | 217–219° C |

EXAMPLE 19

N-[4'-(1'-benzyl) piperidyl]-2-methoxy-4-amino-5-chlorobenzamide methiodide

To a mixture of 3.75 gr of N-[4'-(1'-benzyl) piperidyl]-2-methoxy-4-amino-5-chlorobenzamide (0.01 mol) in 150 ml of anhydrous acetone was added 1.25 ml of methyl iodide (0.02 mol). The mixture was stirred at room temperature overnight and then heated to 45°–50° C. for 3 hours. The insoluble product was recovered by filtration and washed with acetone, to yield 4.5 gr of the product, m.p. 201°–203° C. By a similar procedure, the iodoethylate was obtained, m.p. 205°–207° C.

EXAMPLE 20

100,000 tablets each containing 2.0 mg of N-[4'-(1'-benzyl) piperidyl]-2-methoxy-4-amino-5-chlorobenzamide malate.

Formula

| | |
|---|---|
| N-[4'-(1'-benzyl)-piperidyl]-2-methoxy-4-amino-5-chlorobenzamide malate | 200 g |
| Microcrystalline cellulose | 1870 g |
| Lactose spray dried | 9880 g |
| Carboxymethyl starch | 430 g |
| Sodium stearyl fumarate | 60 g |
| Colloidal Silicon dioxide | 60 g |

Procedure

All the powders are passed through a screen with an opening of 0.6 mm. They are then all mixed in a suitable mixer for 20 minutes and compressed into 125 mg tablets using 6 mm discs and flat beveled punches. The disintegration time of the tablets is about 60 seconds.

EXAMPLE 21

100,000 capsules each containing 2.0 mg of N-[4'-(1'-benzyl) piperidyl]-2-methoxy-4-amino-5-chlorobenzamide malate.

Formula

| | |
|---|---|
| N-[4'-(1'-benzyl)-piperidyl]-2-methoxy-4-amino-5-chloro benzamide malate | 200 g |
| Corn starch | 9600 g |
| Lactose | 10000 g |
| Colloidal silicon dioxide | 100 g |
| Magnesium stearate | 100 g |

Procedure

All the powders are passed through a screen with an opening of 0.6 mm. They are then all mixed in a suitable mixer for 20 minutes and the mixture is distributed into 100,000 capsules of appropriate size using a corresponding filling machine.

EXAMPLE 22

10,000 10 ml bottles each containing 44 mg of N-[4'-(1'-benzyl) piperidyl]-2-methoxy-4-amino-5-chlorobenzamide malate.

Formula

| | |
|---|---|
| N-[4'-(1'-benzyl)-piperidyl]-2-methoxy-4-amino-5-chloro-benzamide malate | 440 g |
| Chlorhexidine acetate | 60 g |
| Propylene glycol | 60000 g |
| Distilled water .s. | 100 liters |

Procedure

The N-[4'-(1'-benzyl) piperidyl]-2-methoxy-4-amino-5-chloro-benzamide malate and the chlorhexidine acetate are dissolved with stirring in 40,000 g of distilled water. The propylene glycol is added and the solution is brought up to volume with distilled water. This solution is distributed into 10,000 10 ml bottles using a corresponding filling machine. The bottles are equipped with a calibrated dropper.

EXAMPLE 23

1,000 bottles each containing 30 mg of N-[4'-(1'-benzyl)-piperidyl]-2-methoxy-4-amino-5-chloro-benzamide malate.

Formula

| | |
|---|---|
| N-[4'-(1'-benzyl)-piperidyl]-2-methoxy-4-amino-5-chloro benzamide malate | 30 g |
| Sorbex | 64000 g |
| Sorbic acid | 150 g |
| Citric acid | 150 g |
| Distilled water .s. | 150 liters |

Procedure

The N-[4'-(1'-benzyl)-piperidyl]-2-methoxy-4-amino-5-chloro-benzamide malate and the sorbic acid are dissolved with stirring in 50,000 g of hot purified water, the Sorbex is added followed by flavoring and citric acid. Once cooled down to room temperature, it is brought up to volume with purified water and distributed into 1,000 bottles using a corresponding filling machine.

EXAMPLE 24

10,000 ampoules each containing 2.0 mg of N-[4'-(1'-benzyl)-piperidyl]-2-methoxy-4-amino-5-chloro-benzamide malate.

Formula

| | |
|---|---|
| N-[4'-(1'-benzyl)-piperidyl]-2-methoxy-4-amino-5-chloro-benzamide malate | 20 g |
| Lactic acid 90% | 400 g |
| Sodium hydroxide 2N. q.s. p.H.=4.7 | |
| Water for Injection q.s. | 20 l |

Procedure

The N-[4'-(1'-benzyl)-piperidyl]-2-methoxy-4-amino-5-chloro-benzamide malate is dissolved with stirring in 15000 g of water for injections, the lactic acid is added, the pH is adjusted to 4.7 with 2 N sodium hydroxide solution and the solution is brought up to volume with water for injection. The resulting solution is filtered through a 0.22 μm pore membrane filter and is distributed in about 10,000 ampoules. The ampoules are closed and sterlized at 121° C. in a steam autoclave for 30 minutes.

EXAMPLE 25

5,000 suppositories each containing 2.5 mg of N-[4'-(1'-benzyl)-piperidyl]-2-methoxy-4-amino-5-chloro-benzamide malate.

Formula

| | |
|---|---|
| N-[4'-(1'-benzyl)-piperidyl]-2-methoxy-4-amino-5-chloro-benzamide malate | 12.5 g |
| Theobroma Oil | 7987.5 g |

Procedure

The N-[4'-(1'-benzyl)-piperidyl]-2-methoxy-4-amino-5-chloro-benzamide malate is passed through a screen with an opening of 0.4 mm and suspended in the theobroma oil previously melted using the minimum amount of heat necessary. The mixture is then poured into suppository molds of a nominal capacity of 1.6 g to produce 5000 suppositories.

EXAMPLE 26

100,000 tablets each containing 11 mgrs of N-[4'-(1'-benzyl) piperidyl]-2-methoxy-4-amino-5-chloro-benzamide hydrochloride monohydrate.

Formula

| | |
|---|---|
| N-[4'-(1'-benzyl-piperidyl]-2-methoxy-4-amino-5-chlorobenzamide hydrochloride monohydrate | 1,100 g |
| Lactose | 5,900 g |
| Microcrystalline cellulose | 6,850 g |
| Carboxymethyl starch | 560 g |
| Hydroxypropylcellulose | 450 g |
| Magnesium stearate | 140 g |
| Ethanol : water 50:50 v/v | q.s. |

Procedure

The finely powdered N-[4'-(1'-benzyl)-piperidyl]-2-methoxy-4-amino-5-chloro-benzamide hydrochloride monohydrate was mixed with the lactose, the carboxymethyl starch and the microcrystalline cellulose in a high intensity Lödige blender. The hydroxypropylcellulose dissolved in the ethanol:water mixture was added and the resulting mass was granulated in the mixer employing the intensifier. The granulate was dried at 40°, passed through a 20 mesh screen, mixed with the magnesium stearate and compressed into tablets each weighing about 150 mg.

The tablets had a disintegration time of about 5 minutes.

EXAMPLE 27

40,000 ampoules each containing 11 mgr of N-[4'-(1'-benzyl) piperidyl]-2-methoxy-4-amino-5-chlorobenzamide hydrochloride monohydrate.

Formula

| | |
|---|---|
| N-[4'-(1'-benzyl)-piperidyl]-2-methoxy-4-amino-5-chlorobenzamide hydrochloride monohydrate | 440 g |
| Sodium chloride | 600 g |
| Benzyl alcohol | 1,200 g |
| Water injectable grade q.s. | 120 l |

Procedure

The N-[4'-(1'-benzyl)-piperidyl]-2-methoxy-4-amino-5-chloro-benzamide hydrochloride monohydrate, the sodium chloride and the benzyl alcohol were dissolved in approximately 100 l. of 70° hot water and the volume was adjusted to 120 l. The solution was filtered through a 0.22μ membrane filter and filled into ampoules each containing about 3.2 ml. The ampoules were closed and sterilized at 120° for 20 minutes in an autoclave, producing approximately 37,000 ampoules.

What is claimed is:

1. N-[4'-(1'-benzyl)-piperidyl]-2-methoxy-4-amino-5-chloro-benzamide or pharmaceutically acceptable salts thereof.

2. The compound of claim 1 in the form of the hydrochloride salt.

3. A pharmaceutical composition for treating gastrointestinal tract disorders in a host comprising the compound of claim 1 and a non-toxic pharmacologically acceptable carrier or diluent therefor.

4. A method for treating gastrointestinal tract disorders which comprises administering in an effective amount the compound of claim 1 to a host.

5. N-[4'-(1'-benzyl) piperidyl]-2-methoxy-4-($\alpha,\alpha,\alpha$-trifluoroacetamido)-5-chlorobenzamide or pharmaceutically acceptable salts thereof.

6. A pharmaceutical composition for treating gastrointestinal tract disorders in a host comprising the compound of claim 5 and a non-toxic pharmacologically acceptable carrier or diluent therefor.

7. A method for treating gastrointestinal tract disorders which comprises administering in an effective amount the compound of claim 5 to a host.

8. N-[4'-(1'-benzyl) piperidyl]-2-methoxy-4-$\alpha$-(1''-piperidyl) acetamido-5-chlorobenzamide or pharmaceutically acceptable salts thereof.

9. A pharmaceutical composition for treating gastrointestinal tract disorders in a host comprising the compound of claim 8 and a non-toxic pharmacologically acceptable carrier or diluent therefor.

10. A method for treating gastrointestinal tract disorders which comprises administering in an effective amount the compound of claim 8 to a host.

* * * * *